(12) United States Patent
Okada et al.

(10) Patent No.: US 9,487,765 B2
(45) Date of Patent: *Nov. 8, 2016

(54) STABILIZED TRANSGLUTAMINASE AND PROCESS FOR PRODUCTION THEREOF

(71) Applicant: Amano Enzyme Inc., Nagoya-shi (JP)

(72) Inventors: Masamichi Okada, Kakamigahara (JP); Yoshiaki Kurono, Kakamigahara (JP); Hitoshi Amano, Kakamigahara (JP); Shotaro Yamaguchi, Kakamigahara (JP)

(73) Assignee: AMANO ENZYME INC., Nagoya-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/923,749

(22) Filed: Oct. 27, 2015

(65) Prior Publication Data

US 2016/0040141 A1 Feb. 11, 2016

Related U.S. Application Data

(62) Division of application No. 14/638,717, filed on Mar. 4, 2015, now Pat. No. 9,217,141, which is a division of application No. 12/864,025, filed as application No. PCT/JP2009/000221 on Jan. 22, 2009, now abandoned.

(30) Foreign Application Priority Data

Feb. 13, 2008 (JP) .................................. 2008-032252

(51) Int. Cl.
C12N 9/10 (2006.01)
C12N 9/96 (2006.01)

(52) U.S. Cl.
CPC ............... *C12N 9/1044* (2013.01); *C12N 9/96* (2013.01); *C12Y 203/02013* (2013.01)

(58) Field of Classification Search
None
See application file for complete search history.

(56) References Cited

U.S. PATENT DOCUMENTS 5,156,956 A 10/1992 Motoki et al.
7,329,521 B2 2/2008 Yuuki et al.

FOREIGN PATENT DOCUMENTS

| EP | 1219713 A1 | 7/2002 |
|---|---|---|
| JP | 04-207194 A | 7/1992 |
| JP | 3281368 | 7/1992 |
| JP | 3651003 | 4/1996 |
| JP | 2001-186884 A | 7/2001 |
| JP | 2004-305010 A | 11/2004 |
| JP | 2005-229807 A | 9/2005 |
| WO | WO-2009/030211 A2 | 3/2009 |

OTHER PUBLICATIONS

Yurimoto et al., Biosci, Biotechnol. Biochem. 68:2058-2069, 2004.
Date et al., J. Biotechnol. 110:219-226, 2004.
Pasternack et al., Eur. J. Biochem. 257:570-573, 1998.
Office Action issued in Japanese Patent Application No. 2009-553353, mailed Feb. 24, 2014.
C. K. Marx et al., "Soluble expression of a pro-transglutaminase from *Streptomyces mobaraensis* in *Escherichia coli*," Enzyme Microb. Technol., vol. 40, 2007, pp. 1543-1550.
Y. Sakai et al., "Secretory production of enzymatically active transglutaminase in the methylotrophic yeast *Candida boidinii*," Abstracts of the Annual meeting of the Society for Biotechnology, Japan, 2001, vol. 2001, pp. 349, 913.
International Search Report dated Feb. 17, 2009, issued on PCT/JP2009/000221.
Supplementary European Search Report dated Aug. 1, 2011, issued for the corresponding European patent application No. 09711348.4.

*Primary Examiner* — David J Steadman
(74) *Attorney, Agent, or Firm* — Locke Lord LLP; James E. Armstrong, IV; Nicholas R. Herrel (57) ABSTRACT

Disclosed is a transglutaminase having excellent stability. Also disclosed is a process for producing the transglutaminase. Specifically disclosed is a stabilized transglutaminase, which has such a structure in which a pro-sequence peptide of transglutaminase is bound to a mature transglutaminase. Also specifically disclosed is a process for producing stabilized transglutaminase, which includes the steps of culturing a microorganism capable of producing transglutaminase under the conditions where transglutaminase can be produced; and separating and collecting matured transglutaminase having a pro-sequence peptide bound thereto from a culture medium.

3 Claims, 7 Drawing Sheets

STABILIZED TRANSGLUTAMINASE AND PROCESS FOR PRODUCTION THEREOF

CROSS-REFERENCE TO RELATED APPLICATIONS

This application is a divisional application of U.S. application Ser. No. 14/638,717 filed Mar. 4, 2015, which is a divisional application of U.S. application Ser. No. 12/864,025 filed Jul. 22, 2010, which is a national stage entry of International Application No. PCT/JP2009/000221 filed Jan. 22, 2009, which claims priority to Japan Application No. 2008-032252 filed Feb. 13, 2008. Each of the foregoing applications is incorporated by reference herein in their entireties for all purposes.

TECHNICAL FIELD

The present invention relates to a transglutaminase, and more particularly to a stabilized transglutaminase having excellent stability against oxidation, temperature stability, and the like.

BACKGROUND ART

Transglutaminases are enzymes that catalyze an acyl transfer reaction of γ-carboxyl amide group of a glutamine residue in a peptide chain. The reaction leads to the formation of ε-(γ-Gln)-Lys cross linking in the intramolecular or intermolecular portion of protein molecules when an ε-amino group of a lysine residue in protein acts as an acyl receptor. Therefore, since the use of the action of a transglutaminase enables protein or peptide to be improved, a transglutaminase of a microbial enzyme derived from the genus *Streptomyces* is used in binding meat and in manufacturing sausage, bean curd, bread, and noodles (see Patent Document 1).

Transglutaminase is a thiol enzyme having cysteine as an active center residue, and is converted into a mature-form via a pro-form in a fermentation process. Therefore, a transglutaminase has poor stability and requires addition of a stabilizer in order to suppress inactivation during manufacture or storage of products.

As a method for improving stability of a transglutaminase during storage, addition of organic acid, inorganic acid, polyphenol, thiol, and sugar alcohol has been proposed (see Patent Document 1). Furthermore, a method for improving stability by adding protein (wheat protein, soybean protein, and the like), or a partial hydrolysate of protein has been developed (see Patent Document 2). Furthermore, a stabilization technique using trehalose has been developed (Patent Document 3).

[Patent Document 1] Japanese Patent Unexamined Publication No. H4-207194

[Patent Document 2] U.S. Pat. No. 3,651,003

[Patent Document 3] Japanese Patent Unexamined Publication No 2004-305010

DISCLOSURE OF THE INVENTION

Problems to be Solved by the Invention

Although various stabilization techniques have been proposed, needs for stabilization of transglutaminases have been still high. As mentioned above, transglutaminases have been widely used in the fields of food. Therefore, in order to avoid unexpected circumstances, it is desirable that extra components are added as little as possible.

Under the above-mentioned background, an object of the present invention is to provide a transglutaminase having excellent stability, a process for producing thereof, and use thereof.

Means to Solve the Problem

Under the above-mentioned circumstances, the present inventors have keenly investigated. As a result, the present inventors have found that an intermediate-form of transglutaminase is present in a culture solution of a transglutaminase-producing strain and succeeded in recovering the intermediate-form. In the further study, it has been clarified that the recovered intermediate-form has a structure in which pro-sequence peptide is bound to mature transglutaminase (mature TGase). On the other hand, as a result of evaluation of stability of the intermediate-form, it has been found that the intermediate-form is more excellent than mature TGase in terms of pH stability, temperature stability, stability against oxidation, and storage stability.

The present invention was made based on the above-mentioned findings, and relates to the below-mention.

[1] A stabilized transglutaminase, including pro-sequence peptide of transglutaminase and a mature transglutaminase, wherein the pro-sequence peptide of transglutaminase is bound to the mature transglutaminase.

[2] The stabilized transglutaminase described in [1], wherein the mature transglutaminase is derived from a microorganism.

[3] The stabilized transglutaminase described in [2], wherein the microorganism is a microorganism of the genus *Streptomyces*.

[4] The stabilized transglutaminase described in [2], wherein the microorganism is *Streptomyces mobaraensis*.

[5] The stabilized transglutaminase described in [1], wherein the mature transglutaminase includes an amino acid sequence set force in SEQ ID NO: 6.

[6] The stabilized transglutaminase described in [1], wherein the pro-sequence peptide is derived from a microorganism.

[7] The stabilized transglutaminase described in [6], wherein the microorganism is a microorganism of the *Streptomyces* genus.

[8] The stabilized transglutaminase described in [6], wherein the microorganism is *Streptomyces mobaraensis*.

[9] The stabilized transglutaminase described in [1], wherein the pro-sequence peptide includes any sequence from the following (1) to (3):

```
                                          (SEQ ID NO: 1)
(1) DNGAGEETKSYAETYRLTADDVANINALNESAPAA;

(SEQ ID NO: 2)
(2) DNGAGEETKSYAETYRLTADDVANINALNESAPAAS;
and (SEQ ID NO: 3)
(3) DNGAGEETKSYAETYRLTADDVANINALNESAPAASS.
```

[10] The stabilized transglutaminase described in any of [1] to [9], wherein the stabilized transglutaminase has higher stability than the mature transglutaminase to which the pro-sequence peptide of transglutaminase is not bound, and the stability is at least one of stability selected from the group consisting of pH stability, temperature stability, stability against oxidation, and storage stability.

[11] An enzyme preparation including the stabilized transglutaminase described in any one of [1] to [10].
[12] A process for producing a stabilized transglutaminase, the process including the steps of:
culturing a microorganism capable of producing transglutaminase under the conditions where transglutaminase can be produced; and
separating and recovering a mature transglutaminase to which pro-sequence peptide is bound from a culture solution.
[13] The process for producing a stabilized transglutaminase described in [12], wherein the microorganism is a microorganism of the genus *Streptomyces*.
[14] The process for producing stabilized transglutaminase described in [12], wherein the microorganism is *Streptomyces mobaraensis*.

BEST MODE OF CARRYING OUT THE INVENTION

Stabilized TGase

A stabilized transglutaminase (stabilized TGase) of the present invention has a structure in which pro-sequence peptide of transglutaminase is bound to mature TGase. That is to say, the stabilized transglutaminase is characterized in that pro-sequence peptide of transglutaminase and mature TGase are included as essential elements, and these elements are bound to each other. With the characteristics, the stabilized TGase of the present invention exhibits higher stability than that of the mature TGase. The term "stability" used herein is intended to include pH stability, temperature stability, stability against oxidation, and storage stability. Therefore, the stabilized TGase of the present invention is more excellent than the mature TGase in terms of at least one stability selected from the group consisting of pH stability, temperature stability, stability against oxidation and storage stability. The stabilized TGase in a preferable embodiment is more excellent than the mature TGase in all of pH stability, temperature stability, stability against oxidation, and storage stability.

By the way, a transglutaminase as secretory protein is translated as a pre-pro-transglutaminase in which a signal sequence (pre-sequence) and a pro-sequence are bound; then the signal sequence is cleaved to be converted into pro-transglutaminase; and subsequently, the pro-sequence peptide is cleaved to be formed into a mature transglutaminase (mature TGase). As shown in the below-mentioned Examples, the present inventors have found the presence of an intermediate-form having a structure in which the cleaved pro-sequence peptide is bound to the mature transglutaminase in the series of process, and also have clarified that the intermediate-form has excellent stability. The stabilized TGase of the present invention is typically obtained as an intermediate-form generated in the above-mentioned process. However, a production process (an obtaining method) is not particularly limited as long as an intermediate-form has a structure in which pro-sequence peptide is bound to mature TGase and has more improved stability than that of the mature TGase. Therefore, stabilized TGase produced by preparing pro-sequence peptide and mature TGase separately and linking both to each other is included in the stabilized TGase of the present invention as long as improvement of stability is observed.

The "pro-sequence peptide" in this specification denotes a part or all of peptide constituting a pro-sequence (that is to say, a sequence provided between a pre-sequence and a mature protein sequence). Three types of peptide are shown as examples of the pro-sequence peptide.

Pro-sequence peptide example 1: Peptide consisting of the sequence of DNGAGEETKSYAETYRLTADDVANINAL-NESAPAA (SEQ ID NO. 1)

Pro-sequence peptide example 2: Peptide consisting of the sequence of DNGAGEETKSYAETYRLTADDVANINAL-NESAPAAS (SEQ ID NO. 2)

Pro-sequence peptide example 3: Peptide consisting of the sequence of DNGAGEETKSYAETYRLTADDVANINAL-NESAPAASS (SEQ ID NO. 3)

The derivation (origin) of the pro-sequence peptide is not particularly limited. Preferably, the pro-sequence peptide is derived from microorganisms. The "pro-sequence peptide derived from microorganisms" include pro-sequence peptide of transglutaminase produced by a microorganism of, for example, the genus *Streptomyces* (see, for example, Japanese Patent Unexamined Publication No. S64-27471), and further, peptide including an amino acid sequence that is the same as that of the pro-sequence peptide (that is to say, a part or an entire part of the pro-sequence of transglutaminase produced by microorganisms). Examples of the amino acid sequences of the full-length pro-sequence of transglutaminase produced by microorganisms are shown in SEQ ID NO: 4 (*Streptomyces mobaraensis*) and SEQ ID NO: 5 (*Streptomyces cinnamoneus*).

Also, the derivation (origin) of the mature TGase as one of the elements of the stabilized TGase of the present invention is not particularly limited. For example, mature TGase produced by a microorganism of, for example, the genus *Streptomyces* (see, for example, Japanese Patent Unexamined Publication No. S64-27471), mature TGase produced by mammalian (see, for example, Japanese Patent Examined Publication No. 111-50382), recombinant (recombination type) mature TGase obtained by the use of recombinant DNA technology (see, for example, Japanese Patent Unexamined Publication Nos. 115-199883 and 2004-97099), and the like, can be used. Preferably, the mature TGase is derived from microorganisms. Examples of the "mature TGase derived from microorganisms" include natural mature TGase produced by microorganisms of the genus *Streptomyces* and the like (see, for example, Japanese Patent Unexamined Publication No. S64-27471), recombinant mature TGase obtained by culturing a transformant into which a transglutaminase gene produced by microorganisms is introduced. Examples of the amino acid sequences of mature TGase derived from microorganisms are shown in SEQ ID NO: 6 (*Streptomyces mobaraensis*) and SEQ ID NO: 7 (*Streptomyces cinnamoneus*).

Preferably, microorganisms as origins of the pro-sequence peptide and/or mature TGase are microorganisms belonging to the genus *Streptomyces*. Examples of microorganisms belonging to the genus *Streptomyces* include *Streptomyces mobaraensis* (old name: *Streptoverticillium mobaraense*) strain No. 140226 (see Japanese Patent Unexamined Publication No. 2005-73628), *Streptomyces lavendulae* strain No. 466 (see U.S. Pat. No. 2,849,773, Patent Document 1), *Streptomyces* sp., No. 83 (see U.S. Pat. No. 2,849,773, Patent Document 1), and the like. Furthermore, it is possible to use mutant strains such as a strain whose productivity is improved by using common methods such as ultraviolet irradiation and NTG (N-methyl-N'-nitrosoguanidine), a strain in which generation of contaminated protein such as protease and amylase is reduced, and a strain in which physiologically active substances such as antibiotics are suppressed or deleted. Furthermore, genetically recombinant strains can be used.

When the recombinant DNA technology is used (that is to say, when a genetically recombinant strain is used), it is possible to obtain a stabilized TGase in which the origin of pro-sequence peptide and the origin of mature TGase are different from each other. Preferably, however, the origin of pro-sequence peptide and the origin of the mature TGase are the same as each other. Stabilized TGase in such a form is obtained as an intermediate-form typically by culturing a transglutaminase-producing strain (a strain originally having a producing ability or a recombinant strain into which a transglutaminase gene is introduced). Hereinafter, one example of the production process of the stabilized TGase in such a form is described.

(Production Process of Stabilized TGase)

Firstly, a microorganism of the genus *Streptomyces* having a transglutaminase-producing ability (for example, *Streptomyces mobaraensis* strain No. 140226) is prepared, and cultured under the conditions where a transglutaminase can be produced. The culture conditions are not particularly limited as long as a transglutaminase can be produced. Specific examples of the culture condition are described in the below-mentioned Examples. A person skilled in art can appropriately change culture conditions.

Examples of a medium include commonly used medium materials including a carbon source such as starch, sucrose, lactose, glycerol, and glucose; a nitrogen source such as peptone, meat extracts, yeast extracts, corn steep liquor, ammonium nitrate, ammonium chloride, and ammonium sulfate; and small amount of metal salts of, for example, monobasic potassium phosphate, dibasic potassium phosphate, magnesium sulfate, manganese sulfate, and calcium carbonate. Furthermore, in order to suppress foaming, defoaming agents can be added if necessary. The culture temperature is generally in the range of 25° C. to 35° C. Furthermore, the culture can be carried out by using various fermentation containers. Generally, aeration stirring is carried out in two to six days. Depending upon the types of strains and fermentation media to be used, culture is not necessarily carried out under these conditions. For example, when feeding of medium materials is carried out, or medium material with high concentration is contained, generally, the culturing time may be further increased. Furthermore, pH of the medium is controlled if necessary.

After the culture is completed, a cell body and the like, is removed from a fermentation mixture by filtration or centrifugation. As the filtration, pressurize filtration with diatom earth added is preferred. Furthermore, it is preferable that the filtration is carried out at not higher than room temperature. The obtained filtrate, that is, a crude enzyme solution of transglutaminase is cooled if necessary. Note here that as described in Eur. J, Biochem., 257, 570-576 (1998), transglutaminase is known to be produced as a precursor. Therefore, in order to convert the transglutaminase into stabilized TGase, a fermentation mixture may be treated by adding an enzyme such as protease and peptidase for a certain period of time. Furthermore, some transglutaminases are known to be present as an oxidation enzyme without having an enzymatic activity. Therefore, it is also desirable that such transglutaminases are converted into an active enzyme by adding an enzyme such as cysteine and glutathione or substances containing thereof. Such activation operations are not necessarily carried out only in purification process, but preferably it is carried out in the early stage of purification.

The crude enzyme solution is concentrated if necessary. The concentration method is not particularly limited, but ultrafiltration capable of carrying out concentration and purification simultaneously is preferred. In general, the crude enzyme solution can be concentrated to about 10 times to 100 times. The degree of concentration is not particularly limited as long as the solution is concentrated to such a concentration that the following process can be carried out. As an ultrafiltration membrane, by considering the molecular weight of TGase (about 38,000), an ultrafiltration membrane having an average pore size with a molecular weight cut-off of 13,000 is preferred. For example, ACP-13000 (Asahi Kasei Corporation) is preferably used. However, even if a membrane having an average pore size with a molecular weight cut-off of 50,000 is used, an enzyme hardly leaks out. Therefore, by selecting membranes as needed, the purification degree can be increased. Although precipitates may be generated during desalitation and concentration, such precipitates can be dissolved by adding appropriate buffer solution or salt solution. Furthermore, a temperature at the time of concentration is not particularly limited, but the temperature is preferably in the range of 10° C. to 30° C. As the temperature is higher, the concentration can be carried out more efficiently. On the contrary, inactivation may occur.

The concentrated solution includes target stabilized TGase (mature TGase to which pro-sequence peptide is bound) and mature TGase. Then, the target stabilized TGase is recovered from the concentrated solution. Hereinafter, an example of recovering the stabilized TGase is described. Firstly, in order to remove contaminated protein, and the like, the concentrated solution is partially purified by pretreatment using ethanol, polyethylene glycol, and the like. Precipitates recovered by the pretreatment are dissolved in an appropriate buffer solution, and then the solution is subjected to dialysis. After dialysis, salting out is carried out by adding salts such as ammonium sulfate and sodium chloride. Thus, mature TGase precipitates. After recovering a supernatant, stabilized TGase in the supernatant is separated and purified by using salting out, column chromatography, centrifugation, and the like. If necessary, desalitation, concentration, or the like, is carried out.

(Enzyme Preparation Containing Stabilized TGase)

An enzyme preparation can be produced by using stabilized TGase. The form of the enzyme preparation of the present invention is not particularly limited. Examples of the form include powder, granule, liquid, capsule, and the like. The enzyme preparation of the present invention contains stabilized TGase as an essential active component. The other components are added arbitrarily. Examples of components that can be contained in the enzyme preparation of the present invention include food excipient, various proteins, various degradation products of protein, various extracts, various salts, various antioxidants, cysteine, glutathione, sodium glutamate, sodium inosinate, sodium guanylate, calcinated shell calcium, and silicon dioxide. Note here that examples of the food excipient include dextrin, branched dextrin, cyclodextrin, glucose, lactose, sucrose, trehalose, maltitol, mannitol, sorbitol, polysaccharide, starch (potato starch, corn starch, and the like), indigestible dextrin, gums, emulsifying agents (sucrose fatty acid ester, lecithin, and the like), pectin, and fats and oils. Examples of the protein include soybean protein, wheat protein, corn protein, milk protein, animal-derived protein, and the like. Examples of the extracts include meat extracts, plant extracts, yeast extracts, and the like. Examples of the salts include chloride salt, phosphate, polyphosphate, pyrophosphate, citrate, lactate, carbonate, and the like. Examples of the antioxidant include L-ascorbate, sodium hydrogen sulfite, and the like.

Example

1. Purification of Stabilized TGase

A medium including 2% soluble starch, 5% sucrose, 2% polypeptone, 0.2% yeast extracts, 0.1% magnesium sulfate, 0.2% dibasic potassium phosphate, and 0.05% Adecanol was used. *Streptomyces mobaraensis* strain No. 140226 as a transglutaminase-producing strain (see Japanese Patent Unexamined Publication No. 2005-73628) was cultured by shaking at 30° C. for two days to obtain 4000 mL of crude enzyme solution. Unless specifically noted, % denotes % by weight (the same is true to each Example mentioned below).

Next, the crude enzyme solution was subjected to desalitation and concentration by using an ultrafiltration membrane (ACP1010, Asahi Kasei Corporation) to obtain 200 mL of concentrated solution. McIlvaine buffer solution (pH 6.0) was added and mixed to the concentrated solution so that the final concentration became 1/10, followed by fractionating with 50% cool ethanol. Recovered precipitates were dissolved in McIlvaine buffer solution at 1/10 concentration (pH 6.0) containing 0.1 M sodium chloride, and then the solution was subjected to dialysis. Then, sodium chloride was added to the dialysate until the concentration of saturated solution was achieved, allowed to stand still at a low temperature for three days, and then supernatant was recovered. The precipitates were crystals of mature TGase (M-TGase). When the precipitates were subjected to recrystallization with a saturated saline solution, M-TGase purified enzyme was obtained. The specific activity of the M-TGase purified enzyme (u/Abs 280 nm) was 19.1. Note here that the amino acid sequence of M-TGase is shown in SEQ ID NO: 6.

On the other hand, ammonium sulfate was added to the recovered supernatant until the concentration of saturated solution was achieved, and precipitates were recovered. The recovered precipitates were dissolved in 20 mM phosphate buffer solution (KPB; pH 7.2), and then dialyzed against the same buffer solution. Next, ammonium sulfate was added to the dialysate so that 1.7 M ammonium sulfate was obtained, which was subjected to Phenyl-Sepharose 6 Fast Flow equilibrated with 20 mM phosphate buffer solution (KPB; pH 7.2) containing 1.7 M ammonium sulfate, washed with 1.7 M ammonium sulfate, and eluted with 1.0 M ammonium sulfate. Thus, the target stabilized TGase (P-TGase) was eluted in the eluted fraction. The specific activity of the thus obtained P-TGase (u/Abs 280 nm) was 7.9. The elution patterns of gel filtration (Sephacryl S-100) was compared between the case in which SDS (sodium dodecyl sulfate) was added and the case in which SDS was not added. The comparison result showed that P-TGase had a structure in which pro-sequence peptide was bound to mature TGase.

The transglutaminase activity was measured according to the method described in Japanese Patent Unexamined Publication No. S64-27471. That is to say, the reaction is carried out by using benzyloxycarbonyl-L-glutaminyl-glycine and hydroxyl amine as a substrate in the absence of $Ca^{2+}$, generated hydroxamic acid is formed into an iron complex under coexistence of trichloroacetic acid. Subsequently, absorbance at 525 nm is measured, a hydroxamic acid amount is obtained from a calibration curve, and the transglutaminase activity is calculated. Hereinafter, detail of the measurement method is described. Firstly, the following reagents A and B are prepared.

Reagent A: 0.2 M Tris-HCl acid buffer solution (pH 6.0), 0.1 M hydroxyl amine, 0.01 M reduced glutathione, 0.03 M benzyloxycarbonyl-L-glutaminyl-glycine Reagent B: 1:1:1 mixture solution of 3N hydrochloric acid, 12% trichloroacetic acid, 5% $FeCl_3$-$6H_2O$ (dissolved in 0.1N-HCl)

The reagent A (0.5 mL) is added to 0.05 mL of enzyme solution, and mixed. The mixture is reacted at 37° C. for 10 minutes. The reagent B is added to the reaction so as to stop the reaction, and to form a Fe complex. Therefore, the absorbance at 525 nm is measured. A control is prepared by the same reaction by using a heat-inactivated enzyme solution, and the absorbance of the control is measured. The difference of absorbance between the enzyme solution and the control is calculated. Additionally, instead of the enzyme solution, L-glutamic acid-γ-monohydroxamic acid is used so as to form a calibration curve, and the amount of the generated hydroxamic acid from the difference of absorbance. The enzymatic activity for generating 1 μmol of hydroxamic acid for one minute is defined as one unit. Unless otherwise noted, the transglutaminase activity is measured by the same measurement method in the following tests.

2. Purification of Pro-Sequence Peptide

Sodium carbonate (5.0 mg) was added to and dissolved in 1.8 mL of P-TGase solution obtained in the above "1," 0.2 mL of 10% (w/v) SDS (sodium dodecyl sulfate) solution was mixed thereto, and the mixture was treated at 37. degree. C. for 30 minutes. The treatment solution (2.0 mL) was subjected to Sephacryl S-100 (column volume: 160 mL) equilibrated with 20 mM KPB (pH 7.2) containing 0.1%

SDS. The absorbance at 280 nm was monitored to recover peaks found around 123 mL of mobile phase amount. The recovered solution was concentrated by centrifugation by using Amicon Ultra (Ultracel-5K) at 4° C. The obtained concentrated solution (sample) was subjected to N-terminal amino acid sequence analysis and mass spectrometry. From the result of the N-terminal amino acid sequence analysis, it was clear that the N terminal of the peptide was DNGA-GEETKS (amino acids 1-10 of SEQ ID NO: 4). On the other hand, as a result of the mass spectrometry, five peaks, m/z (1) 3623.938, (2) 3640.903, (3) 3710.780, (4) 3727.845, and (5) 3813.735 were observed. The (1) and (3) were thought to be deamidation products of (2) and (4). From the results of the N-terminal amino acid sequence analysis and the mass spectrometry, the amino acid sequences of the other three peaks were identified to be:

(SEQ ID NO: 1)
(1) DNGAGEETKSYAETYRLTADDVANINALNESAPAA, (SEQ ID NO: 2)
(2) DNGAGEETKSYAETYRLTADDVANINALNESAPAAS,
and (SEQ ID NO: 3)
(3) DNGAGEETKSYAETYRLTADDVANINALNESAPAASS.

Note here that these sequences correspond to a part of the full length of pro-sequence peptide (SEQ ID NO: 4).

3. Stability Test 1 of P-TGase

Figure 1:
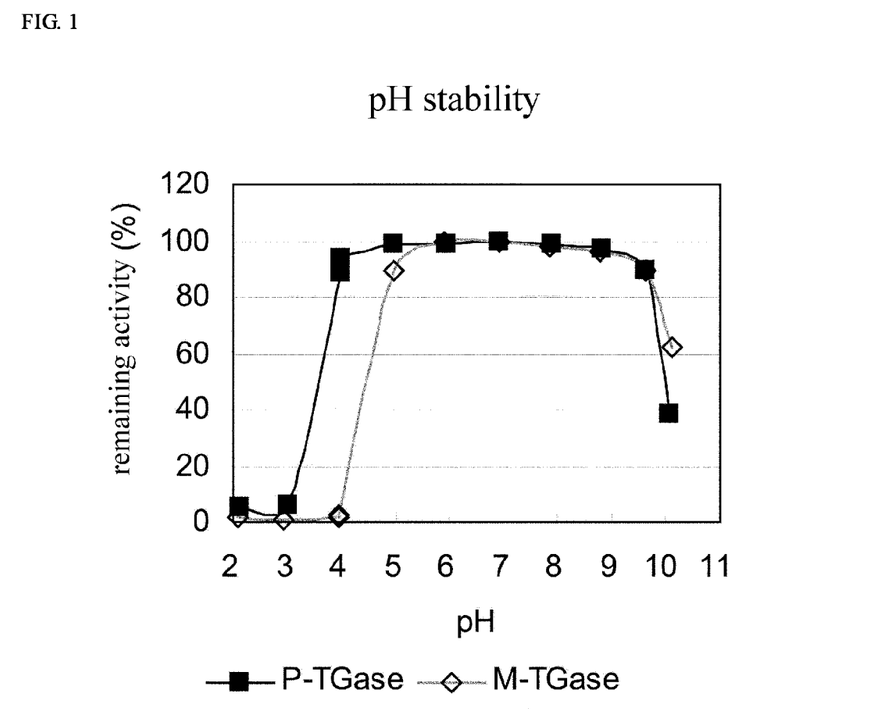
FIG. 1 is a graph showing the comparison of pH stability between stabilized TGase (P-TGase) and mature TGase (M-TGase), in which the abscissa shows pH and the ordinate shows the remaining activity (%).

Comparison of pH stability was carried out between P-TGase and M-TGase. Each enzyme diluent was prepared by using a citric acid-HCl buffer solution with respect to pH 2 to 4 and universal (Britton-Robinson) buffer solution with respect to pH 4 to 11. Each enzyme diluent was treated at 50° C. for one hour, followed by measuring transglutaminase activity. As a result, P-TGase showed 93% remaining activity even under pH4, while the remaining activity of M-TGase under the same condition was 2% (FIG. 1). Thus, P-TGase showed high stability in the acidic condition.

Figure 2:
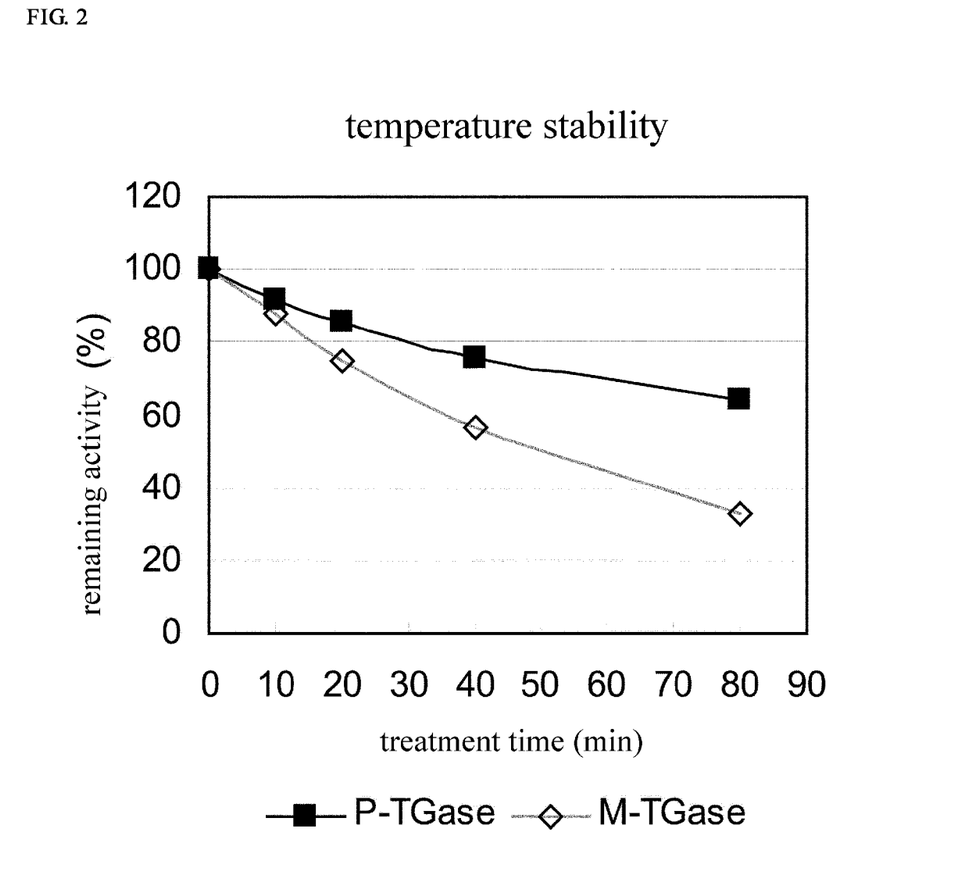
FIG. 2 is a graph showing the comparison of temperature stability between stabilized TGase (P-TGase) and mature TGase (M-TGase), in which the abscissa shows treatment time (minute) and the ordinate shows the remaining activity (%).

On the other hand, comparison of temperature stability was carried out between P-TGase and M-TGase. Each enzyme diluent was prepared with 0.2 M Tris-HCl buffer solution (pH 6.0), and heat-treated at each temperature, followed by measuring the transglutaminase activity. As a result, the remaining activity in the treatment at 50° C. for 80 minutes was 33% in M-TGase and 64% in P-TGase (FIG. 2). Thus, P-TGase showed higher heat stability than M-TGase.

4. Stability Test 2 of P-TGase

Figure 3:
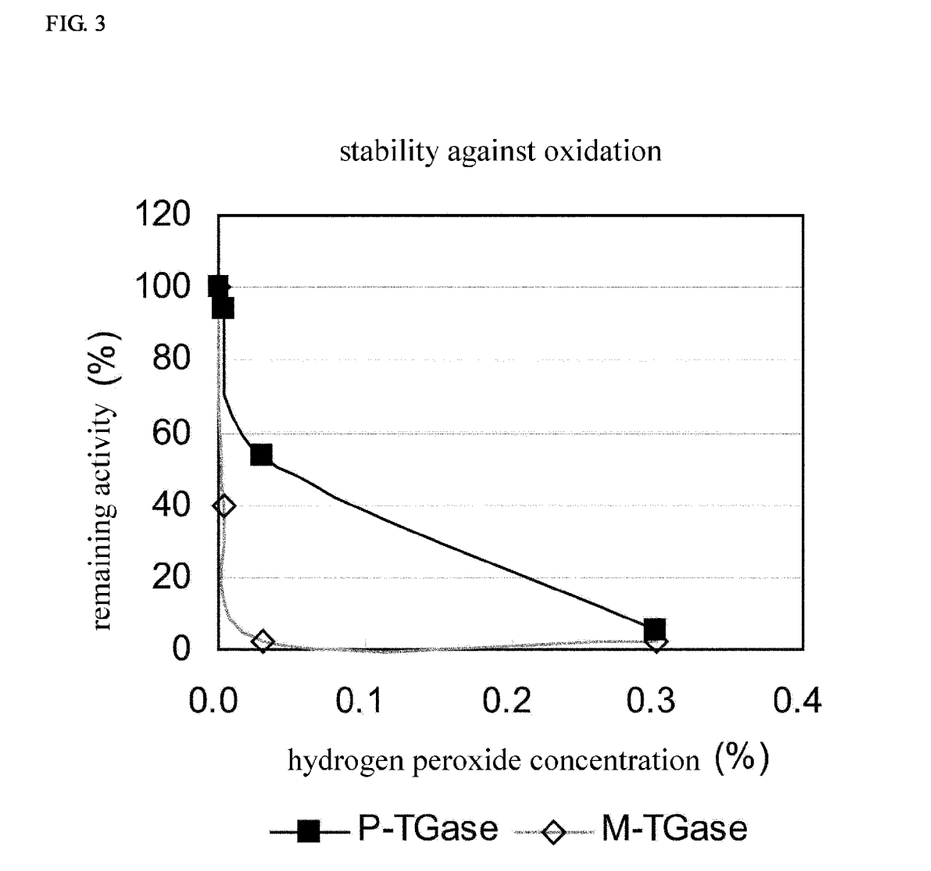
FIG. 3 is a graph showing the comparison of stability against oxidation between stabilized TGase (P-TGase) and mature TGase (M-TGase), in which the abscissa shows hydrogen peroxide concentration (%) and the ordinate shows the remaining activity (%).

In order to evaluate stability to oxidation in a solution (resistance to inactivation by oxidation), an inhibition test (against hydrogen peroxide) was carried out Hydrogen peroxide water (reagent, 30% (w/v)) was appropriately diluted with 0.2 M Tris-HCl buffer solution (pH 6.0), added to an enzyme solution, and treated at 37° C. for 30 minutes. Then, the transglutaminase activities were measured. When the treatment concentration was 0.03% (w/v), the remaining activity was 3% for M-TGase, and 54% for P-TGase (FIG. 3). Thus, P-TGase showed high stability against oxidation in a solution.

5. Stability Test 3 of P-TGase

Figure 4:
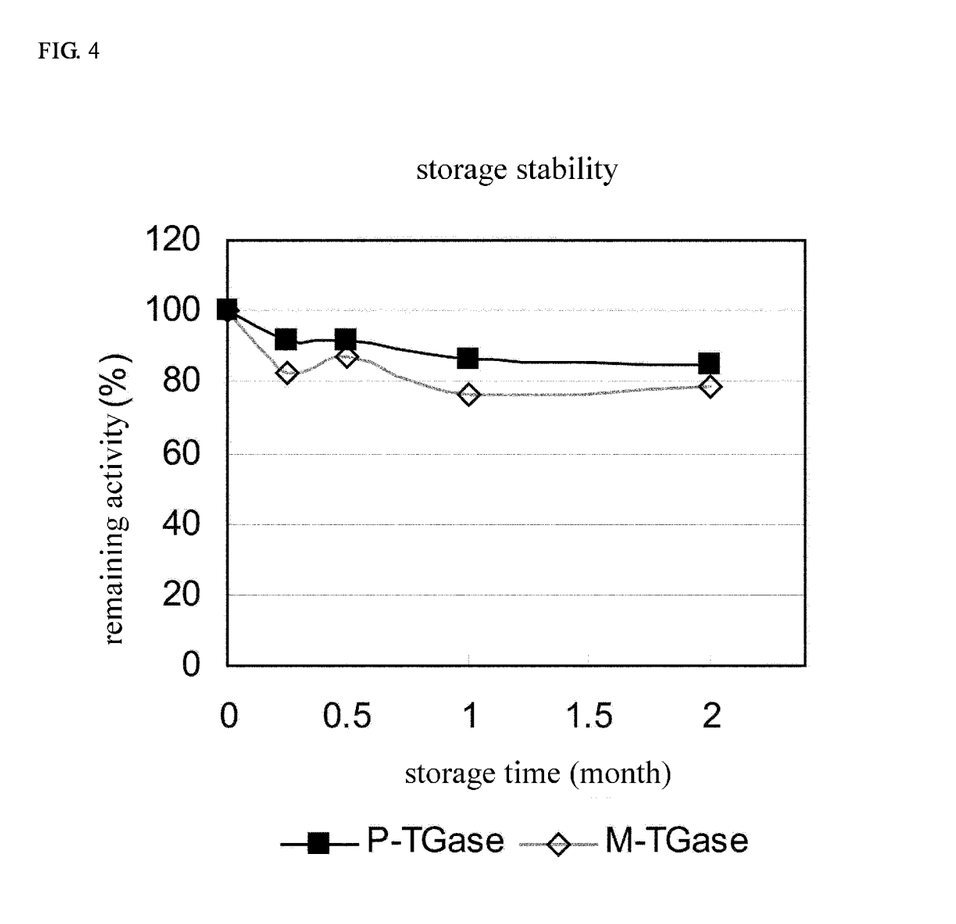
FIG. 4 is a graph showing the comparison of storage stability between stabilized TGase (P-TGase) and mature TGase (M-TGase), in which the abscissa shows storage time (month) and the ordinate shows the remaining activity (%).

The stability in a powder form was evaluated. P-TGase and M-TGase were lyophilized to powder. To the M-TGase powder, dextrin was mixed, so that the transglutaminase activity per weight was made to be the same as that of the P-TGase powder. The storage temperature was 44° C. The remaining activity after two months was 79% for M-TGase, and on the other hand, 85% for P-TGase (FIG. 4). Thus, in the case of a powder state, P-TGase showed high stability.

6. Purification of P-TGase (*Streptomyces lavendulae* Strain No. 466)

A medium including 2% soluble starch, 5% sucrose, 2% polypeptone, 0.2% yeast extracts, 0.1% magnesium sulfate, 0.2% dibasic potassium phosphate, and 0.05% Adecanol was used. *Streptomyces lavendulae* strain No. 466 as a transglutaminase-producing strain (see U.S. Pat. No. 2,849, 773, Japanese Patent Unexamined Publication No. H4-207194) was cultured by shaking at 30° C. for three days to obtain 1500 mL of crude enzyme solution.

Next, the crude enzyme solution was concentrated by using an ultrafiltration membrane (ACP1010, Asahi Kasei Corporation) and 300 mL of concentrated solution was obtained. The concentrated solution was salted out with 80% of saturated solution of ammonium sulfate, precipitates were recovered. The recovered precipitates were dissolved in 20 mM phosphate buffer solution (KPB; pH 7.2), and were further dialyzed against the same buffer solution. The insoluble matters were removed from the dialyzed sample, and the supernatant was similarly subjected to Blue-Sepharose 6 Fast Flow equilibrated with 20 mM phosphate buffer solution (KPB; pH 7.2). The washed fraction in the buffer solution was recovered and dialyzed against 20 mM phosphate buffer solution (KPB; pH6.8) containing 1.7M ammonium sulfate. The dialyzed samples were similarly subjected to Phenyl-Sepharose 6 Fast Flow equilibrated with 20 mM phosphate buffer solution (KPB; pH 6.8) containing 1.7 M ammonium sulfate. The sample was washed with the same buffer solution, and eluted using linear concentration gradient of 1.7-0 M ammonium sulfate. P-TGase was eluted at ammonium sulfate concentration around 1.0 M. Furthermore, M-TGase was eluted at ammonium sulfate concentration around 0.8 M.

7. Stability Test 1 of P-TGase (*Streptomyces lavendulae* Strain No. 466)

Figure 5:
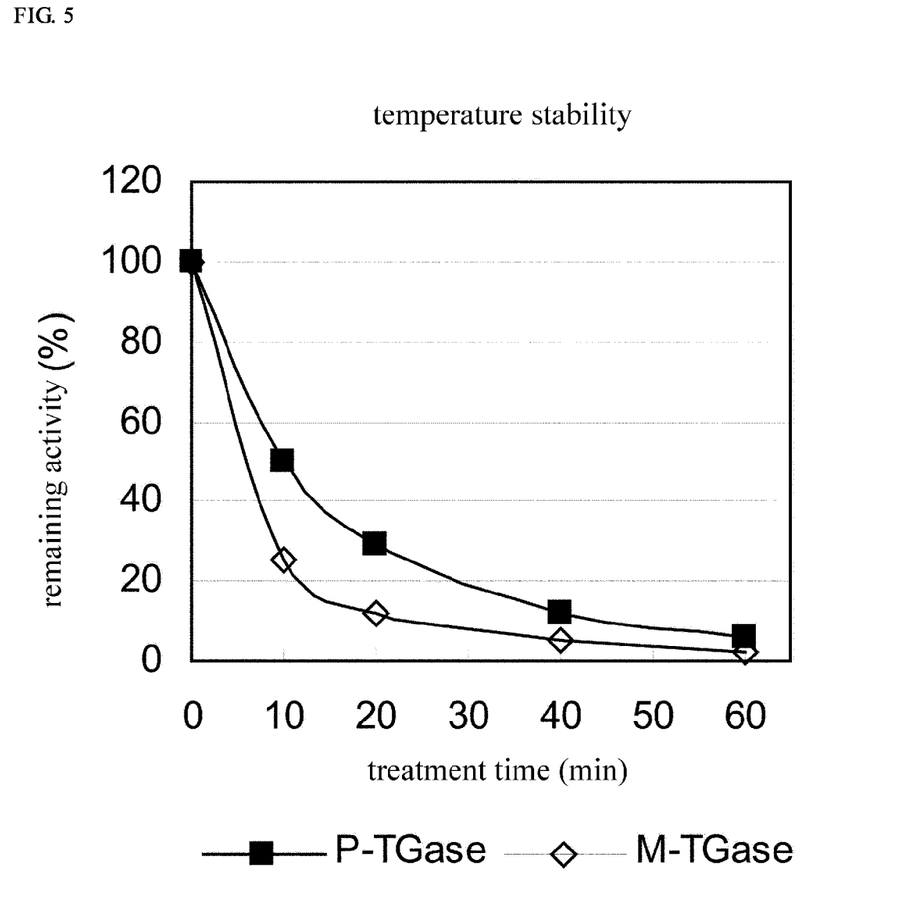
FIG. 5 is a graph showing the comparison of temperature stability between stabilized TGase (P-TGase) and mature TGase (M-TGase), in which the abscissa shows treatment time (min) and the ordinate shows the remaining activity (%).

Comparison of temperature stability was carried out between P-TGase and M-TGase. Each enzyme diluent was prepared with 0.2 M Tris-HCl buffer solution (pH 6.0) and heat-treated at each temperature. Then, each transglutaminase activity was measured. As a result, when treatment was carried out at 50° C. for 20 minutes, the remaining activity was 12% for M-TGase and, on the other hand, 29% for P-TGase (FIG. 5). Thus, P-TGase derived from *Streptomyces lavendulae* strain No. 466 showed higher heat stability than that of M-TGase derived from the same strain.

8. Stability Test 2 of P-TGase (*Streptomyces lavendulae* Strain No. 466)

Figure 6:
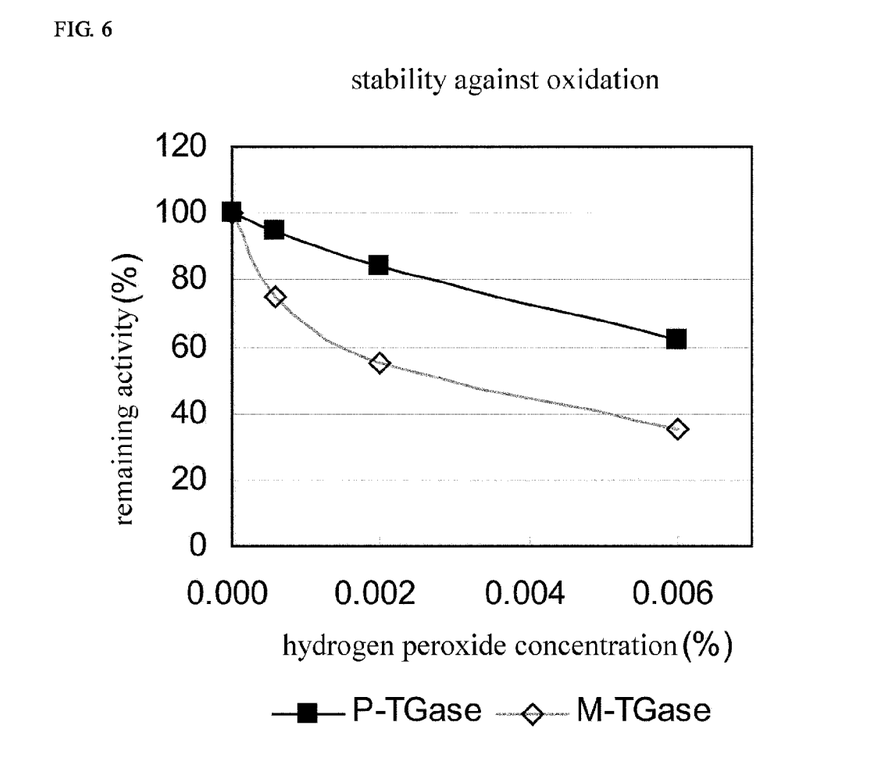
FIG. 6 is a graph showing the comparison of stability against oxidation between stabilized TGase (P-TGase) and mature TGase (M-TGase), in which the abscissa shows hydrogen peroxide concentration (%) and the ordinate shows the remaining activity (%).

In order to evaluate stability to oxidation in a solution (resistance to inactivation by oxidation), an inhibition test (against hydrogen peroxide) was carried out. Hydrogen peroxide water (reagent, 30% (w/v)) was appropriately diluted with 0.2 M Tris-HCl buffer solution (pH 6.0), and the diluted solution was added to an enzyme solution and treated at 37° C. for 15 minutes. Then, the transglutaminase activities were measured. When the treatment concentration was 0.06% (w/v), the remaining activity was 35% for M-TGase, and 62% for P-TGase (FIG. 6). Thus, P-TGase derived from *Streptomyces lavendulae* strain No. 466 showed high stability against oxidation in a solution.

9. Preparation of Pro-Transglutaminase

A medium including 2% soluble starch, 5% sucrose, 2% polypeptone, 0.2% yeast extracts, 0.1% magnesium sulfate, 0.2% dibasic potassium phosphate, and 0.05% Adecanol was used. *Streptomyces mobaraensis* strain No. 140226 as a transglutaminase-producing strain (see Japanese Patent Unexamined Publication No. 2005-73628) was cultured by shaking at 30° C. for two days to obtain 1500 mL of crude enzyme solution. Next, the crude enzyme solution was concentrated by using an ultrafiltration membrane (ACP1010, Asahi Kasei Corporation) to obtain 150 mL of concentrated solution. The concentrated solution was purified according to the method based on document information (Eur. J. Biochem. 257, 570-576 (1998)), and thus pro-transglutaminase was obtained.

10. Preparation of P-TGase (Conversion from Pro-Transglutaminase by Protease Treatment)

A pro-transglutaminase solution was dialyzed against 50 mM Hepes buffer solution (pH 7.4) containing 150 mM sodium chloride to obtain the dialysis sample (Abs. 280 nm=1.8). Dispase II (Roche) was added to the dialysis sample so that the final concentration of the treated solution was 0.08 u/mL, and treated at 30° C. for 60 minutes. Thus, P-TGase was prepared. The reaction was stopped by diluting the reaction solution with 0.2 M Tris-HCl buffer solution (pH 6.0) containing 5 mM EDTA at the operating concentration described in the following "11." On the other hand, similar to P-TGase, as M-TGase to be used in the following "11," a sample that had been treated with Dispase II was used.

11. Stability Test of P-TGase (Protease-Treated Product)

Figure 7:
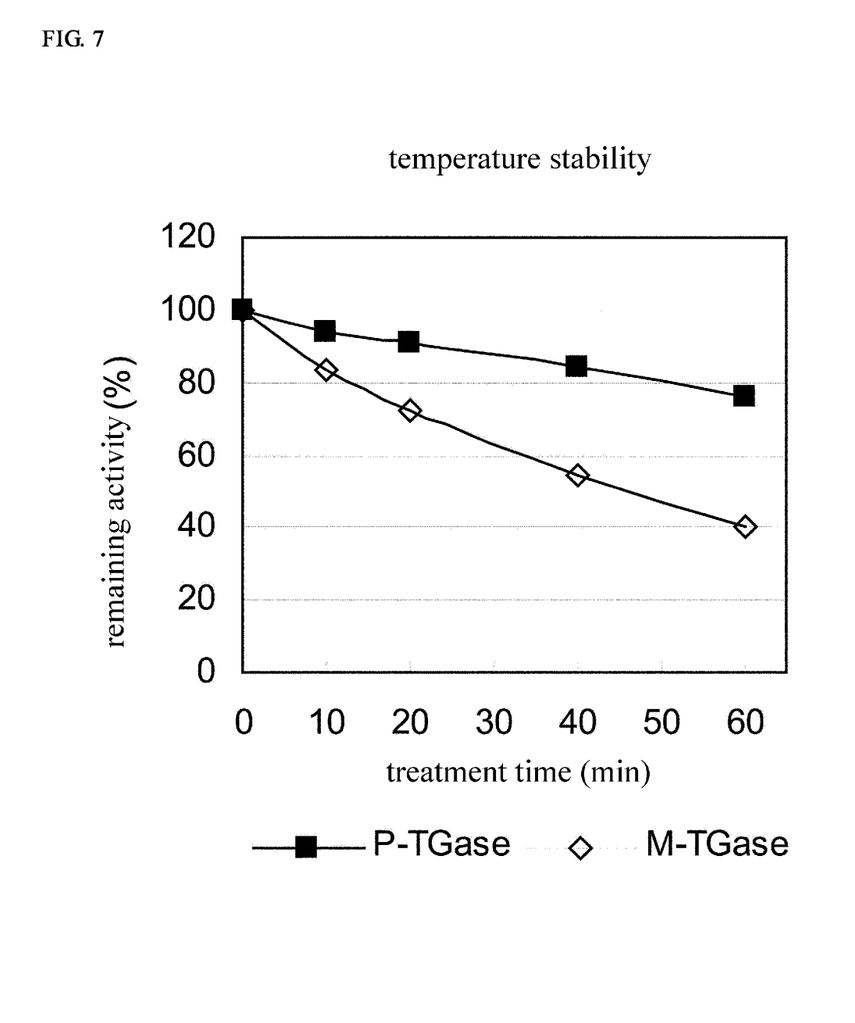
FIG. 7 is a graph showing the comparison of temperature stability between stabilized TGase (P-TGase) and mature TGase (M-TGase), in which the abscissa shows treatment time (min) and the ordinate shows the remaining activity (%).

Comparison of temperature stability was carried out between P-TGase and M-TGase. Each enzyme diluent was prepared with 0.2 M Tris-HCl buffer solution (pH 6.0), and heat-treated at each temperature. Each transglutaminase activity was measured. As a result, when treatment was carried out at 50° C. for 60 minutes, the remaining activity was 41% for M-TGase and, on the other hand, 76% for P-TGase (FIG. 7). Thus, P-TGase obtained by protease treatment also showed higher heat stability than that of M-TGase. Consequently, P-TGase in the above "10" obtained by protease treatment was thought to be the same substance as P-TGase in the above "1."

INDUSTRIAL APPLICABILITY

A stabilized transglutaminase of the present invention has more excellent pH stability, temperature stability, and the like, as compared with a mature transglutaminase. The stabilized transglutaminase of the present invention may be used in binding meat, and in manufacturing sausage, bean curd, bread, and noodles.

The present invention is not limited to the description of the above exemplary embodiments and Examples. A variety of modifications, which are within the scopes of the following claims and which can be easily achieved by a person skilled in the art, are included in the present invention.

Contents of the theses, Publication of Patent Applications, Patent Publications, and other published documents referred to in this specification are herein incorporated by reference in its entity.

[Sequence Listing]

The invention claimed is:

1. A method for stabilizing a mature transglutaminase, the method comprising
providing a purified transglutaminase pro-sequence peptide consisting of the amino acid sequence of SEQ ID NO: 1, 2, or 3 and a purified mature transglutaminase consisting of the amino acid sequence of SEQ ID NO: 6; and
contacting the transglutaminase pro-sequence peptide with the mature transglutaminase to non-covalently bind the transglutaminase pro-sequence peptide to the mature transglutaminase to thereby stabilize the mature transglutaminase.

2. The method according to claim 1, wherein the transglutaminase pro-sequence peptide is purified from *Streptomyces mobaraensis*.

3. The method according to claim 1, wherein the mature transglutaminase is purified from *Streptomyces mobaraensis*.

* * * * *

```
SEQUENCE LISTING

<160> NUMBER OF SEQ ID NOS: 7

<210> SEQ ID NO 1
<211> LENGTH: 35
<212> TYPE: PRT
<213> ORGANISM: Streptomyces mobaraensis

<400> SEQUENCE: 1

Asp Asn Gly Ala Gly Glu Glu Thr Lys Ser Tyr Ala Glu Thr Tyr Arg
1               5                   10                  15

Leu Thr Ala Asp Asp Val Ala Asn Ile Asn Ala Leu Asn Glu Ser Ala
            20                  25                  30

Pro Ala Ala
        35

<210> SEQ ID NO 2
<211> LENGTH: 36
<212> TYPE: PRT
<213> ORGANISM: Streptomyces mobaraensis

<400> SEQUENCE: 2

Asp Asn Gly Ala Gly Glu Glu Thr Lys Ser Tyr Ala Glu Thr Tyr Arg
1               5                   10                  15

Leu Thr Ala Asp Asp Val Ala Asn Ile Asn Ala Leu Asn Glu Ser Ala
            20                  25                  30
```

```
Pro Ala Ala Ser
        35

<210> SEQ ID NO 3
<211> LENGTH: 37
<212> TYPE: PRT
<213> ORGANISM: Streptomyces mobaraensis

<400> SEQUENCE: 3

Asp Asn Gly Ala Gly Glu Glu Thr Lys Ser Tyr Ala Glu Thr Tyr Arg
1               5                   10                  15

Leu Thr Ala Asp Asp Val Ala Asn Ile Asn Ala Leu Asn Glu Ser Ala
            20                  25                  30

Pro Ala Ala Ser Ser
        35

<210> SEQ ID NO 4
<211> LENGTH: 45
<212> TYPE: PRT
<213> ORGANISM: Streptomyces mobaraensis

<400> SEQUENCE: 4

Asp Asn Gly Ala Gly Glu Glu Thr Lys Ser Tyr Ala Glu Thr Tyr Arg
1               5                   10                  15

Leu Thr Ala Asp Asp Val Ala Asn Ile Asn Ala Leu Asn Glu Ser Ala
            20                  25                  30

Pro Ala Ala Ser Ser Ala Gly Pro Ser Phe Arg Ala Pro
        35                  40                  45

<210> SEQ ID NO 5
<211> LENGTH: 54
<212> TYPE: PRT
<213> ORGANISM: Streptomyces cinnamoneus

<400> SEQUENCE: 5

Gly Asp Gly Glu Glu Lys Gly Ser Tyr Ala Glu Thr His Gly Leu Thr
1               5                   10                  15

Ala Asp Asp Val Glu Ser Ile Asn Ala Leu Asn Glu Arg Ala Leu Thr
            20                  25                  30

Leu Gly Gln Pro Gly Lys Pro Pro Lys Glu Leu Pro Pro Ser Ala Ser
        35                  40                  45

Ala Pro Ser Arg Ala Pro
    50

<210> SEQ ID NO 6
<211> LENGTH: 331
<212> TYPE: PRT
<213> ORGANISM: Streptomyces mobaraensis

<400> SEQUENCE: 6

Asp Ser Asp Asp Arg Val Thr Pro Pro Ala Glu Pro Leu Asp Arg Met
1               5                   10                  15

Pro Asp Pro Tyr Arg Pro Ser Tyr Gly Arg Ala Glu Thr Val Val Asn
            20                  25                  30

Asn Tyr Ile Arg Lys Trp Gln Gln Val Tyr Ser His Arg Asp Gly Arg
        35                  40                  45

Lys Gln Gln Met Thr Glu Glu Gln Arg Glu Trp Leu Ser Tyr Gly Cys
    50                  55                  60

Val Gly Val Thr Trp Val Asn Ser Gly Gln Tyr Pro Thr Asn Arg Leu
65              70                  75                  80
```

```
Ala Phe Ala Ser Phe Asp Glu Asp Arg Phe Lys Asn Glu Leu Lys Asn
                85                  90                  95

Gly Arg Pro Arg Ser Gly Glu Thr Arg Ala Glu Phe Glu Gly Arg Val
            100                 105                 110

Ala Lys Glu Ser Phe Asp Glu Glu Lys Gly Phe Gln Arg Ala Arg Glu
        115                 120                 125

Val Ala Ser Val Met Asn Arg Ala Leu Glu Asn Ala His Asp Glu Ser
130                 135                 140

Ala Tyr Leu Asp Asn Leu Lys Lys Glu Leu Ala Asn Gly Asn Asp Ala
145                 150                 155                 160

Leu Arg Asn Glu Asp Ala Arg Ser Pro Phe Tyr Ser Ala Leu Arg Asn
                165                 170                 175

Thr Pro Ser Phe Lys Glu Arg Asn Gly Gly Asn His Asp Pro Ser Arg
            180                 185                 190

Met Lys Ala Val Ile Tyr Ser Lys His Phe Trp Ser Gly Gln Asp Arg
        195                 200                 205

Ser Ser Ser Ala Asp Lys Arg Lys Tyr Gly Asp Pro Asp Ala Phe Arg
210                 215                 220

Pro Ala Pro Gly Thr Gly Leu Val Asp Met Ser Arg Asp Arg Asn Ile
225                 230                 235                 240

Pro Arg Ser Pro Thr Ser Pro Gly Glu Gly Phe Val Asn Phe Asp Tyr
                245                 250                 255

Gly Trp Phe Gly Ala Gln Thr Glu Ala Asp Ala Asp Lys Thr Val Trp
            260                 265                 270

Thr His Gly Asn His Tyr His Ala Pro Asn Gly Ser Leu Gly Ala Met
        275                 280                 285

His Val Tyr Glu Ser Lys Phe Arg Asn Trp Ser Glu Gly Tyr Ser Asp
290                 295                 300

Phe Asp Arg Gly Ala Tyr Val Ile Thr Phe Ile Pro Lys Ser Trp Asn
305                 310                 315                 320

Thr Ala Pro Asp Lys Val Lys Gln Gly Trp Pro
                325                 330

<210> SEQ ID NO 7
<211> LENGTH: 330
<212> TYPE: PRT
<213> ORGANISM: Streptomyces cinnamoneus

<400> SEQUENCE: 7

Ser Asp Asp Arg Glu Thr Pro Pro Ala Glu Pro Leu Asp Arg Met Pro
1               5                   10                  15

Glu Ala Tyr Arg Ala Tyr Gly Gly Arg Ala Thr Thr Val Val Asn Asn
            20                  25                  30

Tyr Ile Arg Lys Trp Gln Gln Val Tyr Ser His Arg Asp Gly Lys Lys
        35                  40                  45

Gln Gln Met Thr Glu Glu Gln Arg Glu Lys Leu Ser Tyr Gly Cys Val
    50                  55                  60

Gly Val Thr Trp Val Asn Ser Gly Pro Tyr Pro Thr Asn Arg Leu Ala
65                  70                  75                  80

Phe Ala Ser Phe Asp Glu Asn Lys Tyr Lys Asn Asp Leu Lys Asn Thr
                85                  90                  95

Ser Pro Arg Pro Asp Glu Thr Arg Ala Glu Phe Glu Gly Arg Ile Ala
            100                 105                 110

Lys Gly Ser Phe Asp Glu Gly Lys Gly Phe Lys Arg Ala Arg Asp Val
```

-continued

```
            115                 120                 125
Ala Ser Val Met Asn Lys Ala Leu Glu Asn Ala His Asp Glu Gly Thr
        130                 135             140
Tyr Ile Asn Asn Leu Lys Thr Glu Leu Thr Asn Asn Asn Asp Ala Leu
145                 150                 155                 160
Leu Arg Glu Asp Ser Arg Ser Asn Phe Tyr Ser Ala Leu Arg Asn Thr
                165                 170                 175
Pro Ser Phe Lys Glu Arg Asp Gly Gly Asn Tyr Asp Pro Ser Lys Met
            180                 185                 190
Lys Ala Val Ile Tyr Ser Lys His Phe Trp Ser Gly Gln Asp Gln Arg
            195                 200                 205
Gly Ser Ser Asp Lys Arg Lys Tyr Gly Asp Pro Glu Ala Phe Arg Pro
        210                 215                 220
Asp Gln Gly Thr Gly Leu Val Asp Met Ser Lys Asp Arg Ser Ile Pro
225                 230                 235                 240
Arg Ser Pro Ala Lys Pro Gly Glu Gly Trp Val Asn Phe Asp Tyr Gly
                245                 250                 255
Trp Phe Gly Ala Gln Thr Glu Ala Asp Ala Asp Lys Thr Thr Trp Thr
            260                 265                 270
His Gly Asp His Tyr His Ala Pro Asn Ser Asp Leu Gly Pro Met His
            275                 280                 285
Val His Glu Ser Lys Phe Arg Lys Trp Ser Ala Gly Tyr Ala Asp Phe
290                 295                 300
Asp Arg Gly Ala Tyr Val Ile Thr Phe Ile Pro Lys Ser Trp Asn Thr
305                 310                 315                 320
Ala Pro Ala Lys Val Glu Gln Gly Trp Pro
                325                 330
```